(12) United States Patent
Takahashi

(10) Patent No.: US 12,268,625 B2
(45) Date of Patent: Apr. 8, 2025

(54) PINCER NAIL CORRECTION TOOL

(71) Applicant: JPS CORPORATION, Tokyo (JP)

(72) Inventor: Tomoyuki Takahashi, Tokyo (JP)

(73) Assignee: JPS CORPORATION, Tokyo (JP)

(*) Notice: Subject to any disclaimer, the term of this patent is extended or adjusted under 35 U.S.C. 154(b) by 297 days.

(21) Appl. No.: 16/314,469

(22) PCT Filed: Jun. 16, 2017

(86) PCT No.: PCT/JP2017/022255
§ 371 (c)(1),
(2) Date: Dec. 31, 2018

(87) PCT Pub. No.: WO2018/138945
PCT Pub. Date: Aug. 2, 2018

(65) Prior Publication Data
US 2019/0167465 A1 Jun. 6, 2019

(30) Foreign Application Priority Data
Jan. 27, 2017 (JP) ................ 2017-013250

(51) Int. Cl.
*A61F 5/11* (2006.01)

(52) U.S. Cl.
CPC ................... *A61F 5/11* (2013.01)

(58) Field of Classification Search
CPC ........ A61F 5/11; A61F 5/018; A61F 5/05875; A61F 13/105
USPC ........................................ 602/31
See application file for complete search history.

(56) References Cited

U.S. PATENT DOCUMENTS

| 2,405,547 | A | * | 8/1946 | Armagost | A61F 5/11 602/31 |
| 2,632,441 | A | | 3/1953 | Tuve | |
| 3,032,032 | A | * | 5/1962 | Gifford | A61F 5/11 63/11 |
| 8,517,966 | B2 | * | 8/2013 | Erdogan | A61F 5/11 606/86 R |
| 2009/0078277 | A1 | * | 3/2009 | Uemura | A61F 5/11 132/333 |
| 2009/0204045 | A1 | | 8/2009 | Kim | |

(Continued)

FOREIGN PATENT DOCUMENTS

| CN | 1695571 A | 11/2005 |
| CN | 201189225 | 2/2009 |

(Continued)

OTHER PUBLICATIONS

Russian Office Action issued on Jun. 30, 2020, in connection with corresponding RU Application No. 2020103040/14 (004726) (13 pp., including machine-generated English translation).

(Continued)

*Primary Examiner* — Ophelia A Hawthorne
*Assistant Examiner* — Michael Milo
(74) *Attorney, Agent, or Firm* — Maier & Maier, PLLC

(57) ABSTRACT

To achieve prevention of cracking at the time of attachment, wide coping with different nail widths for individuals, reduction in manufacturing costs, maintenance of attached state on free edges, and the like. An ingrown nail corrector includes a corrective body, a support hole, and a clamping portion, and is attached to a free edge of a nail to correct the ingrown nail.

5 Claims, 9 Drawing Sheets

(56) References Cited

U.S. PATENT DOCUMENTS

| | | | |
|---|---|---|---|
| 2010/0228173 A1* | 9/2010 | Ishida | A61F 5/11 602/5 |
| 2012/0197172 A1 | 8/2012 | Ogawa | |
| 2012/0238930 A1* | 9/2012 | Yoshino | A61F 5/11 602/31 |
| 2013/0102942 A1* | 4/2013 | Tanaka | B21D 5/16 602/31 |

FOREIGN PATENT DOCUMENTS

| | | | | |
|---|---|---|---|---|
| CN | 102614039 | A | | 8/2012 |
| CN | 203483556 | U | | 3/2014 |
| CN | 204016580 | U | | 12/2014 |
| CN | 104921788 | A | | 9/2015 |
| CN | 204766080 | U | | 11/2015 |
| CN | 204971772 | | | 1/2016 |
| DE | 3330813 | A1 | | 3/1985 |
| EP | 1 849 442 | A1 | | 10/2007 |
| EP | 2561841 | A1 | * | 3/2013 ............... A61F 5/11 |
| JP | 2007-244852 | A | | 9/2007 |
| JP | 2007-289712 | A | | 11/2007 |
| JP | 2014113322 | A | * | 6/2014 |
| JP | 2016-41234 | A | | 3/2016 |
| JP | 2016041234 | A | * | 3/2016 |
| JP | 2016165436 | A | * | 9/2016 |
| KR | 20150137289 | A | * | 12/2015 |
| TW | 201238576 | A | | 10/2012 |
| WO | WO-2008039028 | A1 | * | 4/2008 ............... A61F 5/11 |
| WO | 2013027256 | A1 | | 2/2013 |

OTHER PUBLICATIONS

International Search Report dated Aug. 15, 2017 of corresponding International Application No. PCT/JP2017/022255; 1 page.

Office Action issued on Jul. 22, 2020 in corresponding Chinese Application No. 201780049652.6; 16 pages including English-language translation.

Extended European search report issued on Feb. 4, 2020, in corresponding European patent application No. 17893511.0; 8 pages.

Chinese Office Action issued on Mar. 26, 2021, in connection with corresponding CN Application No. 201780049652.6 (10 pp., including machine-generated English translation).

\* cited by examiner

PINCER NAIL CORRECTION TOOL

TECHNICAL FIELD

The present invention relates to an ingrown nail corrector which corrects an ingrown nail of a toe.

BACKGROUND ART

As a conventional method for correcting an ingrown nail of a toe, there is a method called a wire method, which is known as a method most frequently used for an ingrown nail correction.

In the wire method, holes are drilled at both right and left end sides of a free edge of a nail extending to about 2 mm to 3 mm (an edge on a tip side of the nail separated from the toe), and while bending a wire having elasticity in which an axis returns from a curved state of the axis to a linear state with respect to the holes, both end portions of the wire are inserted into the holes.

In the ingrown nail correction method, in a state in which the wire is bent and inserted, a force for returning the wire axis linearly acts on the wire, and by utilizing the linearly returning force, both end sides of the nail are expanded to right and left sides to correct the ingrown nail.

However, in many cases, the ingrown nail is brittle, and when a force of expanding both the right and left end sides of the nail from side to side acts on the hole due to returning of the wire inserted in the hole to a linear shape, there are problems of a breakage of the nail around the hole, and breakage of the nail when opening the hole.

In order to avoid these problems, as described in the following Patent Document 1, an ingrown nail corrector that corrects the ingrown nail without opening a hole in the nail has been proposed (see FIGS. 2, 3, and 4).

The ingrown nail corrector illustrated in FIGS. 2 and 3 is configured so that a claw facing a correction plate in a vertical direction protrudes from one side end of the correction plate. FIG. 2 illustrates a configuration in which the correction plate is used as a back side of the free edge, the claw is used as a front side of the free edge, and the corrector is attached by being fitted to the free edge in a clamped manner. FIG. 3 illustrates a configuration in which the correction plate is used as the front side, the claw is used as the back side, and the corrector is attached by being fitted to the free edge in a clamped manner.

In addition, in the ingrown nail corrector illustrated in FIG. 4, the correction plate is bent at the center portion, hooks fitted to the end edge of the free edge are included in both ends of the correction plate, and the ingrown nail corrector is attached by being fitted to the end edge of the free end.

CITATION LIST

Patent Document

Patent Document 1: JP 2007-244852 A

SUMMARY OF THE INVENTION

Problem to be Solved by the Invention

According to the ingrown nail corrector of the related art illustrated in FIGS. 2 and 3, by clamping the free edge with the correction plate and the claw, the corrector can be attached to the nail without opening the hole, and it is possible to correct the ingrown nail, while lifting the free edge by elasticity of the correction plate at the time of attachment.

Further, according to the ingrown nail corrector of the related art illustrated in FIG. 4, by fitting the hooks to both end edges of the free edge and clamping the free edge, the ingrown nail corrector can be attached to the nail without opening the hole, and it is possible to correct the ingrown nail by maintaining the state in which the correction plate expands the free edge at the time of attachment.

Further, in the ingrown nail corrector disclosed in Patent Document 1, as illustrated in FIGS. 2, 3, and 4, by doubly folding back the claw portion and the hook portion, the claw and the hook are formed in a spring shape, and in a state of the ingrown nail corrector being attached to the free edge, a spring force is applied in the clamping direction to maintain the attached state.

However, since the above-described ingrown nail corrector of the related art is a molded article which is formed to have a predetermined shape and a length corresponding to a length in a width direction (a right-left direction) of the nail as illustrated in [0028], and FIGS. 2, 3, and 4, there is a problem that it is difficult to cope with a nail width that varies from individual to individual.

In order to make the ingrown nail corrector cope with the individually different nail widths, there is a method for preparing ingrown nail correctors of a plurality of sizes in which the length along the nail width direction is different in units of mm. However, since it is not possible to make an ingrown nail corrector cope with every nail width as a ready-made product in terms of higher manufacturing costs, the size of the ingrown nail corrector is restricted to a limited size to a certain extent, but since the nail width differs for each individual as described above, there is a problem that the size does not match at the time of attachment.

In the ingrown nail corrector of the related art, the attached state is maintained by clamping the free edge using the spring force of the claw and the hook. However, due to the user's walking or attachment and detachment of socks, there is a problem of occurrence of deviation or detachment of the ingrown nail corrector with respect to the free edge.

In the ingrown nail corrector of the related art illustrated in FIG. 4, since the bent portion protruding from the front side of the nail is caught in the attached state, the ingrown nail corrector is easily removed by walking of the user or attachment and detachment of socks, etc., the corners of the bent portion are caught inside socks and shoes, and the socks and shoes may be damaged.

In contrast to the ingrown nail corrector of the related art illustrated in FIG. 4, in the ingrown nail corrector of the related art illustrated in FIGS. 2 and 3, at the time of beginning of attachment of the free edge, since the correction plate and the claw extend along the back side and the front side of the free edge, it is difficult to disengage the ingrown nail corrector as compared with the ingrown nail corrector of the related art illustrated in FIG. 4, and it is considered that the inner sides of socks and shoes are not damaged. However, since the ingrown nail corrector is clamped by the spring force against the free edge, the ingrown nail corrector eventually slips off and comes off.

In order to prevent deviation or detachment of the ingrown nail corrector of the related art illustrated in FIGS. 2 and 3, it is conceivable to fix the ingrown nail corrector to the free edge, using an adhesive or the like. However, when the ingrown nail corrector is fixed to the free edge, there is a problem that the ingrown nail cannot be corrected.

Hereinafter, on the basis of FIGS. 9(a) and 9(b), the corrected state of the ingrown nails will be described, and the problems when an ingrown nail corrector 100 is fixed to a free edge 200 will be described. FIG. 9(a) illustrates a state at the beginning of the correction of the ingrown nail, and FIG. 9(b) illustrates a state of the latter half of the correction of the ingrown nail.

When correcting the ingrown nail, the ingrown nail corrector 100 is kept attached, and the bending of the free edge 200 that has become the ingrown nail is gradually flattened and corrected by the repulsive force of a correction plate 101.

In such a corrected state, at the beginning of the correction of the ingrown nail corrector 100, the correction plate 101 is bent to follow the bending of the free edge 200, and the position of a claw 102 on a front side 201 of the free edge 200 is in a position corresponding to the bending of the correction plate 101.

In the operation in which the correction plate 101 is gradually flattened due to its own repulsive force from the initial state of correction to the end of correction, the correction plate 101 and the claw 102 which clamp the free edge 200 shift to a flattened state, while sliding along the nail width direction with respect to the free edge 200, and at the time of shifting to the flattened state, the correction plate 101 and the claw 102 press and expand the bending of the free edge 200 due to the ingrown nail.

That is, since the correction plate 101 and the claw 102 slide with respect to the free edge 200, the ingrown nail corrector 100 performs an operation in which the correction plate 101 is flattened in the attached state, and can perform correction of the ingrown nail by this operation.

On the other hand, when the correction plate 101 or the claw 102 is fixed to the free edge 200 in order to prevent detachment of the ingrown nail corrector 100, since sliding of the correction plate 101 and the claw 102 with respect to the free edge 200 is prevented, the correction plate 101 cannot be flattened from a bent state.

Therefore, when the correction plate 101 or the claw 102 is fixed to the free edge 200 in order to prevent detachment of the ingrown nail corrector 100, there is a structural problem that the ingrown nail cannot be corrected.

In addition, if the ingrown nail corrector 100 is not loosened to some extent even by the clamping force to the free edge 200, the sliding of the correction plate 101 and the claw 102 will be inhibited, and the correction of the ingrown nail cannot be performed normally. Thus, there is also a problem that it is not possible to strengthen the clamping force.

Therefore, there is a demand for an ingrown nail corrector that solves each of the aforementioned problems in which it is possible to prevent cracking of the nail at the time of attachment, to widely cope with to different nail widths for individuals, to reduce the manufacturing cost, to maintain the attached state with respect to the free edge, and to correct normal ingrown nails while the attached state is maintained.

Means for Solving Problem

In order to solve the aforementioned problems, the invention adopts the following means.

An ingrown nail corrector which is attached to a free edge of a nail to correct an ingrown nail, the ingrown nail corrector including a corrective body, a support hole, and a clamping portion. The corrective body is formed to have a length in a longitudinal direction to be equal to or larger than a nail width of the free edge, using a material having elasticity in which a repulsive force is generated against a force in a direction of flexure. The support hole has an axis parallel to the longitudinal direction of the corrective body. The corrective body is inserted in a freely slidable manner with the longitudinal direction of the corrective body parallel to an axis of the support hole. The clamping portion includes a fixing plate having one end protruding to be fixed to the support hole with a width direction parallel to the axis of the support hole, a support plate which is disposed to face the fixing plate while being spaced apart in a thickness direction of the fixing plate with the width direction thereof parallel to the axis of the support hole, a contact protrusion integrally formed with the support plate or the fixing plate and formed so as to be located between the support plate and the fixing plate, an insertion port secured between the fixing plate and an end portion of the support plate on the support hole side, and a connecting portion which connects the fixing plate and the support plate at an end portion on the protruding side and has elasticity in which a repulsive force is generated against a force in a direction in which the support plate separates from the fixing plate with expansion of the insertion port.

BRIEF DESCRIPTION OF DRAWINGS

FIG. 9(a) illustrates a state at the time of beginning of correction of the ingrown nail, and FIG. 9(b) illustrates a state of a latter half of correction of the ingrown nail.

MODE(S) FOR CARRYING OUT THE INVENTION

Figure 1:
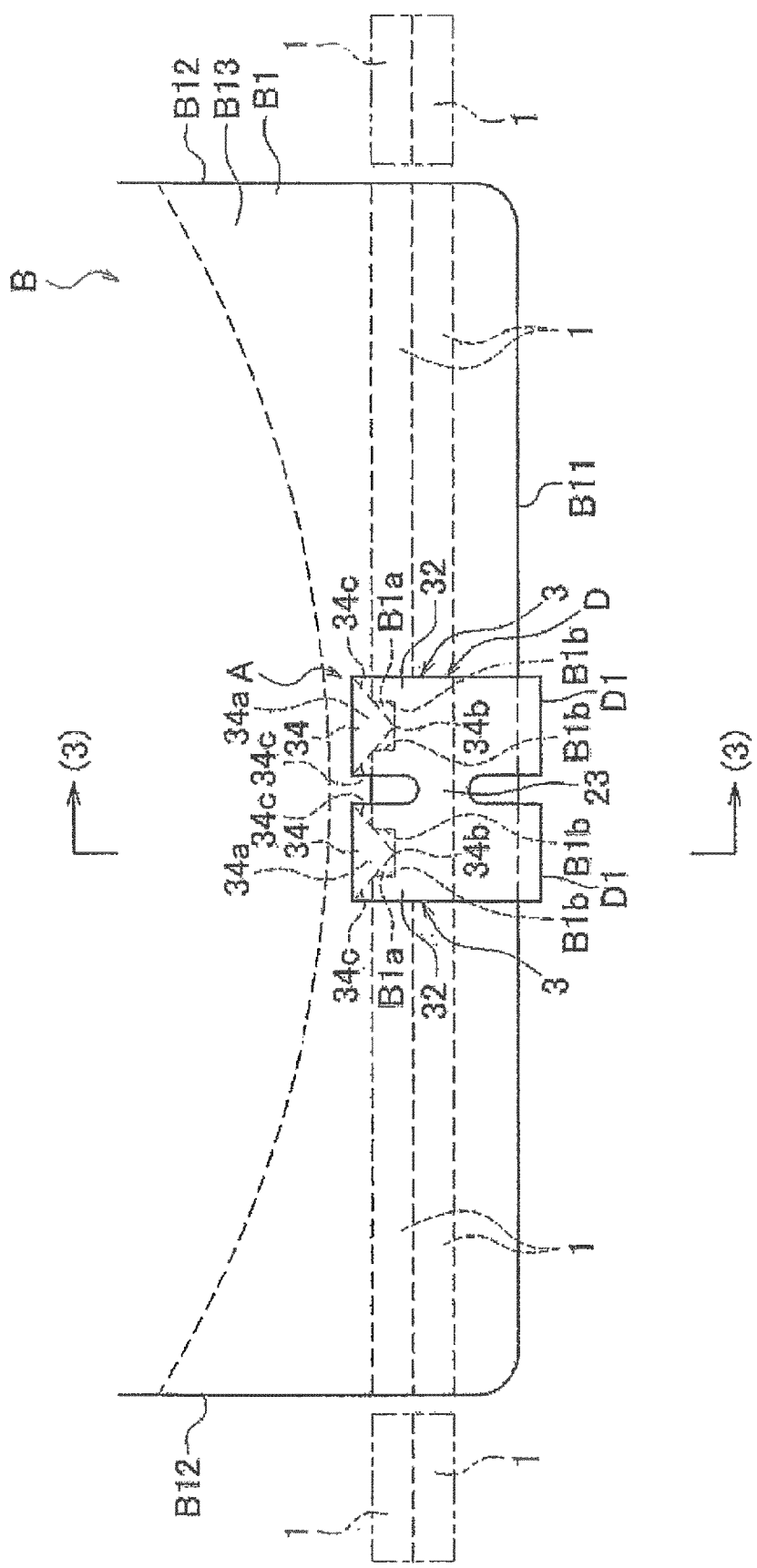
FIG. 1 is a plan view of an ingrown nail corrector according to a first embodiment of the invention.
Figure 2:
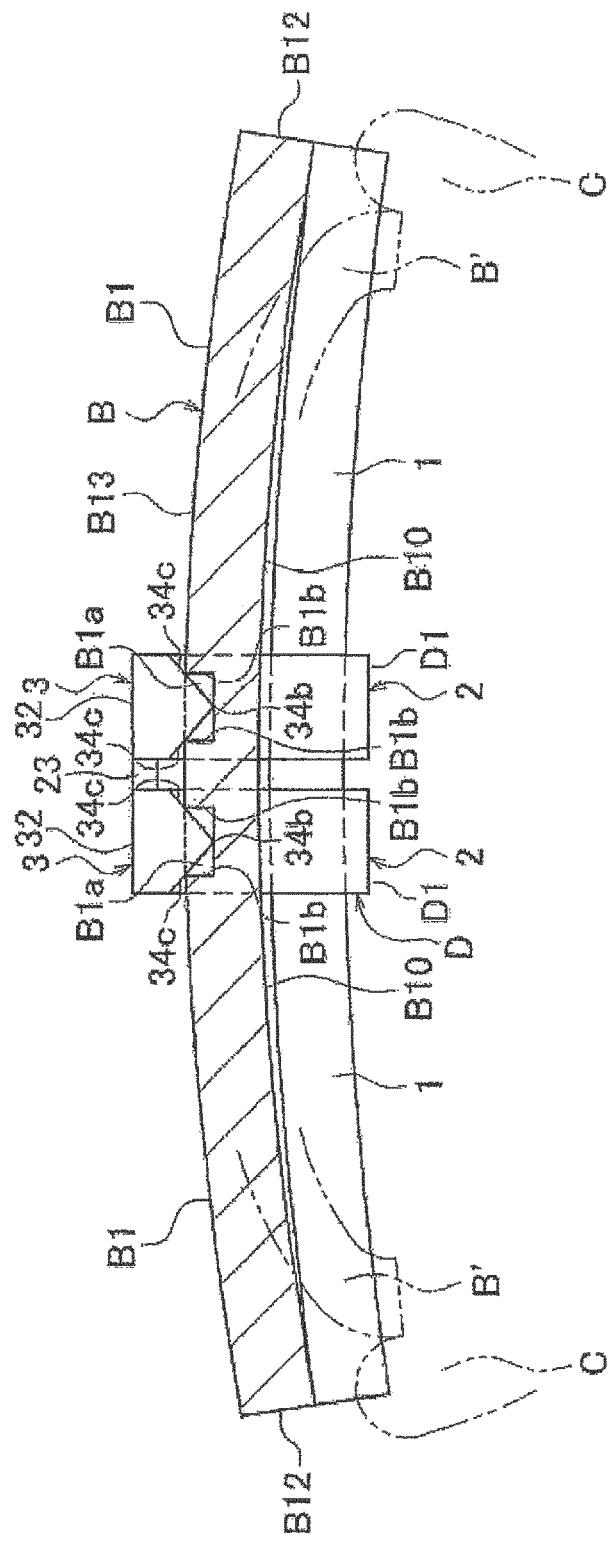
FIG. 2 is a rear view of FIG. 1 illustrating only a free edge in cross section.

Hereinafter, an ingrown nail corrector A according to a first embodiment of the invention will be described with reference to FIGS. 1 to 4. Each embodiment described below does not limit the invention.

The ingrown nail corrector A includes two corrective bodies 1, a support hole 2 that supports the corrective bodies 1 to freely slide in an axial direction, and a clamping portion 3 which is provided integrally with the support hole 2 and is attached to a free edge B1 of a nail B.

In a state in which the corrective body 1 is arranged on a surface (hereinafter referred to as "back side") B10 of the free edge B1 of the nail B on the side of a toe C side along the width of the nail B, by fitting the clamping portion 3 from the side of a tip B11 of the free edge B1 with respect to the free edge B1, the ingrown nail corrector A is attached to the nail B and is configured so that the correction of an ingrown nail B' (see FIG. 2) is started in the attached state.

The corrective body 1 is a linear body made of a material having elasticity such as a metal material or a shape memory alloy material, and due to the elasticity, a repulsive force is generated against flexure of the axis of the corrective body 1. By utilizing the repulsive force, the corrective body 1 supports the free edge B1 to lift the free edge B1 from the back side B10 of the nail B, which makes it possible to maintain the corrected state of the ingrown nail.

Two corrective bodies 1 are collectively covered with a resin film 10, and when the corrective bodies 1 come into contact with the free edge B1 during correction of the ingrown nail B', by relaxing the contact pressure with the resin film 10, it is possible to suppress occurrence of breakage or cracking of the free edge B1 due to the contact pressure.

The length (the length along the width direction of the free edge B1) of the corrective body 1 in the axial direction is set to be longer than a right-left width of the free edge B1, and the corrective body 1 protrudes from the right and left edges B12 and B12 of the free edge B1 in the state of being attached to the free edge B1. However, by cutting the protruding portion, the length of the corrective body 1 in the axial direction is adjusted to the length that does not protrude from the right and left edges B12 and B12 of the free edge B1 in the width direction (see FIG. 2).

Further, the number of corrective bodies 1 is not limited to two as exemplified but may be one to three or more. The number of corrective bodies 1 is the number that can be placed on the back side B10 of the free edge B1, and may be the number in which the repulsive force capable of maintaining the corrected state of the ingrown nail B' is generated.

Further, the corrective body 1 is not limited to a linear body, and may be a plate-like body. For example, an element in which a metal material or a shape memory alloy material having elasticity is formed into a plate shape may be adopted.

The support hole 2 and the clamping portion 3 are formed in a clip D integrally formed by performing various machining such as cutting, bending and folding on a thin metal plate having elasticity.

Specifically, the clip D includes two clip portions D1 formed so that the support hole 2 and the clamping portion 3 are continuous along the longitudinal direction of the free edge B1 (an extension direction of the free edge B1), the clip portions D1 are arranged as a pair so as to be aligned in parallel in the width direction of the free edge B1, and the clip portions D1 and D1 aligned in parallel are integrated via a connecting plate 23.

In the invention, without being limited to the configuration in which the support hole 2 and the clamping portion 3 are integrally formed, the support hole 2 and the clamping portion 3 may be separately formed, and both of them may be fixed and integrated via the connecting plate 23. Further, the invention is not limited to an aspect in which the support hole 2 and the clamping portion 3 are divided.

Figure 3:
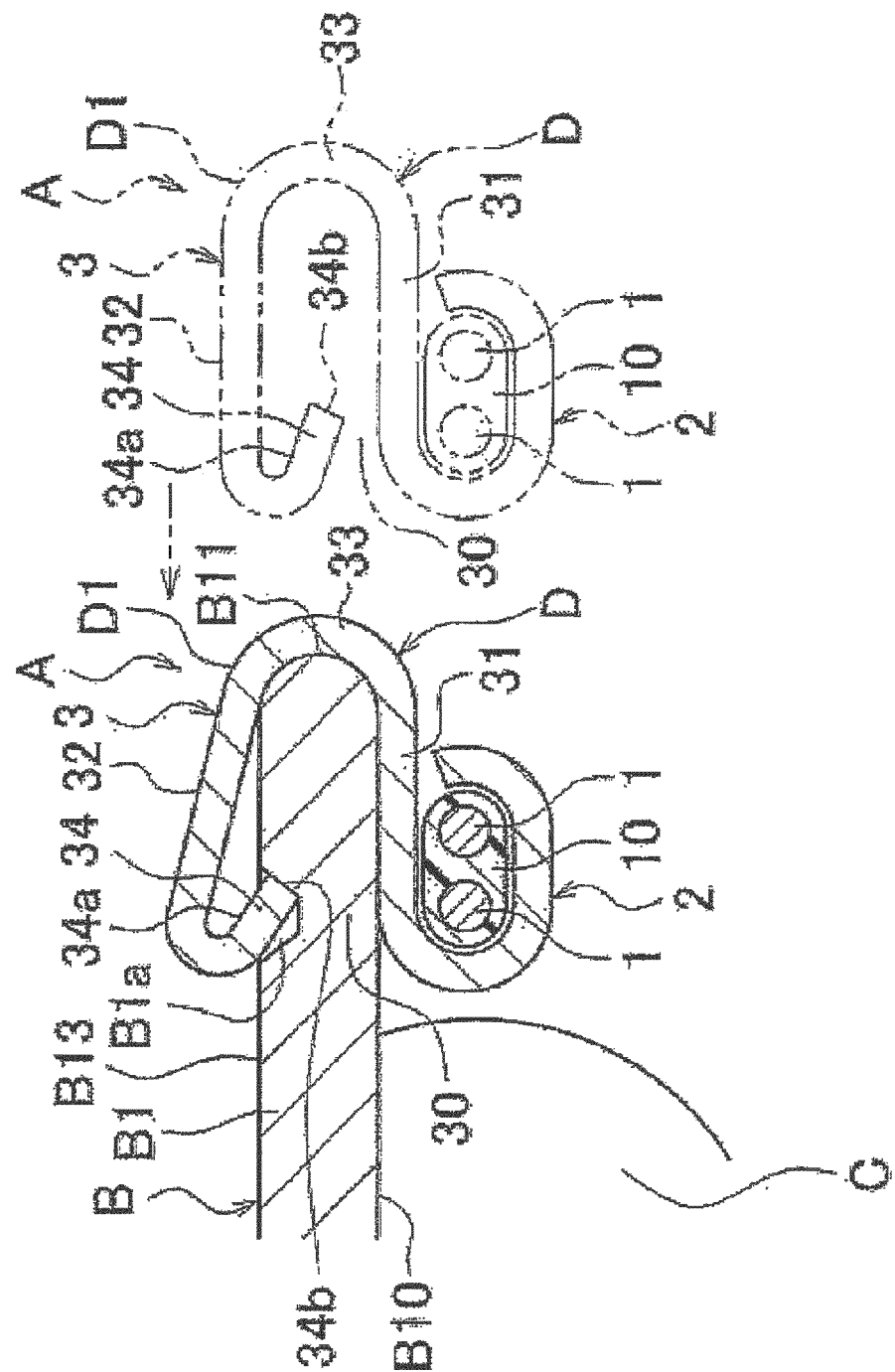
FIG. 3 is a cross-sectional view taken along line (3)-(3) of FIG. 1.
Figure 4:
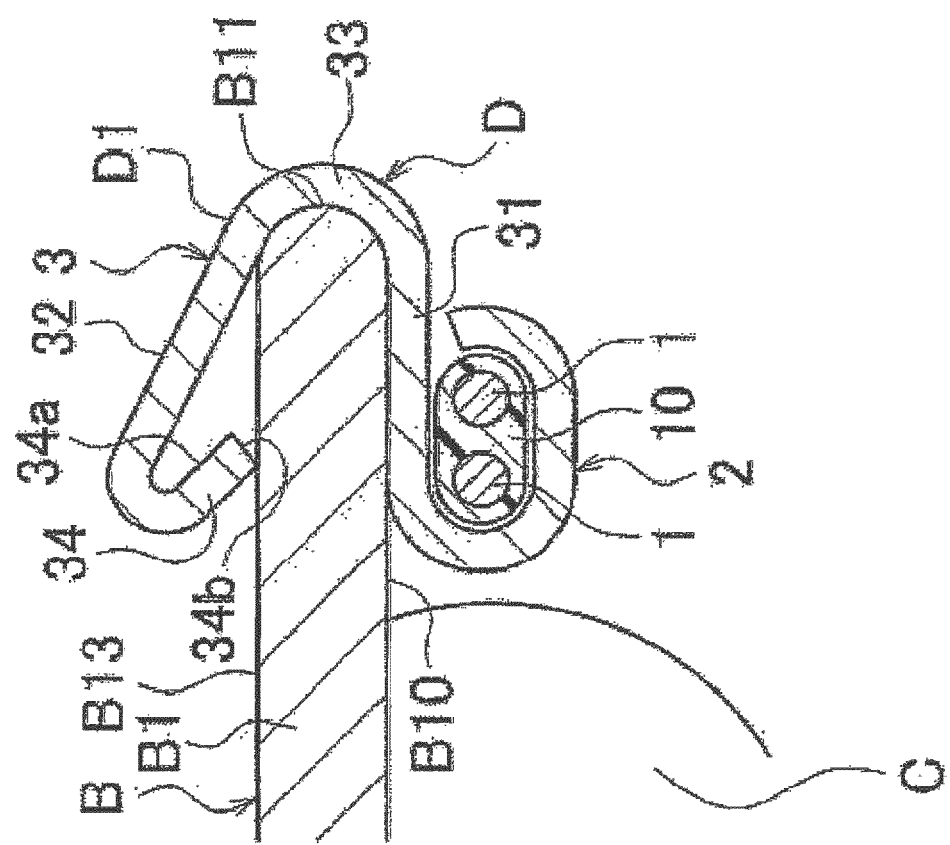
FIG. 4 illustrates a state in which the ingrown nail corrector is attached to a free edge, without providing a latching groove in FIG. 3.

The support hole 2 has an axis parallel to the axis of the corrective body 1, and is inserted so that the corrective body 1 can slide freely in the axial direction and is inserted to be removable, and the support hole 2 is formed in an oblong cross section which is long in the front-rear direction such that the two corrective bodies 1 are arranged in the front-rear direction along the radial direction (see FIG. 3).

The cross-sectional shape of the support hole 2 is a shape corresponding to the cross-sectional shape of the corrective body 1 when the corrective body 1 is in the form of a plate, and when the number of the corrective bodies 1 is one, the corrective body 1 supported as a circular cross section does not shift back and forth.

As the form of the corrective body 1, as illustrated, it is preferable that two linear members are arranged side by side in the radial direction and are covered with the resin film 10, or are formed in a plate shape. By setting the cross-sectional shape of the support hole 2 to a form suitable for the cross-sectional shape of these corrective bodies 1, since rotation of the corrective body 1 in the support hole 2 can be prevented, the attaching work can be carried out extremely smoothly.

The clamping portion 3 has the same length in the width direction as the axial length of the support hole 2, and is formed in a U-shaped spring shape which is continuous in a direction protruding forward from the circumferential end of the support hole 2 bent in a circular oval cross-sectional shape.

The clamping portion 3 has a fixing plate 31 continuously formed from the circumferential end of the support hole 2 with an end portion facing the support hole 2 as an insertion port 30, a support plate 32 disposed to face the fixing plate 31 in the thickness direction of the fixing plate 31, a connecting portion 33 having a U-shaped cross section which connects the fixing plate 31 and the support plate 32 on the protruding side, and a contact protrusion 34 provided at the end portion of the support plate 32 on the side of the insertion port 30 to protrude toward the fixing plate 31.

The insertion port 30 is set to have a width of the fixing plate 31 along the thickness direction (width in the height direction) that is greater than the thickness of the free edge B1.

The connecting portion 33 has a spring force in which a repulsive force in the direction of closing the insertion port 30 is generated against a force in a direction in which the support plate 32 is separated from the fixing plate 31 (the direction in which the insertion port 30 is expanded) by the opening movement of the insertion port 30 in the thickness direction of the fixing plate 31.

In addition, the connecting portion 33 is not limited to a U-shaped cross section, but may be of any form as long as it has a spring force that generates a repulsive force in a direction of closing the insertion port 30 with respect to the opening movement of the insertion port 30.

The contact protrusion 34 is formed as an inclined surface 34a which gradually approaches the fixing plate 31 side as it goes from the end portion of the support plate 32 on the side of the insertion port 30 to the side of the connecting portion 33 and inclines to narrow the space between the fixing plate 31 and the support plate 32.

Further, the contact protrusion 34 is formed in a tapered shape with a sharp tip 34b of the end portion on the protruding side, as a tapered shape from both widthwise edge portions to the end portion on the protruding side, and the tip 34b is caught in a latching groove B1a provided on the front side of the free edge B1 at the time of attachment.

Attachment of the ingrown nail corrector A to the free edge B1 is carried out by fitting the clamping portion 3 to the free edge B1 in a state in which the corrective body 1 is disposed on the back side B10 of the free edge B1.

The clamping portion 3 positions the fixing plate 31 on the side of the back side B10 of the free edge B1, positions the support plate 32 on the side of a front side B13 of the free edge B1 and clamping portion 3, and can fit the clamping portion 3 to the free edge B1, by pushing the insertion port 30 from the tip B11 to the free edge B1 in a state of making the insertion port 30 directly face the tip B11 of the free edge B1.

In the fitting operation of the clamping portion 3, when the inclined surface 34a comes into contact with the free edge B1 and the inclined surface 34a moves to the rear side (the toe C side) of the free edge B1, the support plate 32 moves in the height direction along the thickness of the free edge B1 against the repulsive force, and brings the contact protrusion 34 to the front side B13 of the free edge B1.

In the fitting of the clamping portion 3, the corrective body 1 is positioned on the back side B10 of the free edge B1 while being bent, and both end portions in the width direction which are the ingrown nails of the free edge B1 are expanded, and while keeping the corrective body 1 along the backside B10 of the free edge B1, fitting is performed.

When the fitting of the clamping portion 3 is completed, a repulsive force against the deflection of the corrective body 1 can be allowed to act on the back side B10 of the free edge B1 so that the right and left end portions B12 and B12 of the expanded free edge B1 do not become the ingrown nail B' again.

Further, a certain degree of range along the axial direction of the circumferential surface of the corrective body 1 supports the free edge B1 in a state of being in contact with the back side B10 of the free edge B1. Accordingly, it is possible to support the free edge B1 so as to lift the right and left end portions B12 and B12 of the free edge B1 in a state in which the entire region of the corrective body 1 comes into contact with the entire region of the back side B10 of the free edge B1 in the width direction.

In a state in which the clamping portion 3 is fitted and the corrective body 1 is positioned on the back side B10 of the free edge B1, both end portions of the corrective body 1 protrude outward from the right and left end portions B12, B12 of the free edge B1. However, by cutting the protruding portion of the corrective body 1 (indicated by an imaginary line of FIG. 1) at a portion which is flush with the right and left end portions B12, B12 of the free edge B1, it is possible to dispose the corrective body 1 without protruding from the right and left end portions B12, B12 of the free edge B1, thereby making it possible to wear the socks and shoes as usual.

Before fitting of the clamping portion 3, the front side of the free edge B1 is cut to form a latching groove B1a to which the tip 34b of the contact protrusion 34 is latched, and in a state in which the clamping portion 3 is fitted to the free edge B1, the tip 34b is latched to the latching groove B1a.

The depth of the latching groove B1a may be a slight depth enough to make it difficult for the clamping portion 3 to be detached from the free edge B1 due to catching of the tip 34b. With this degree of depth, it is easy to remove the clamping portion 3, and it is possible to easily cut without generating breakage, cracking, etc. of the free edge B1.

According to the ingrown nail corrector A having the aforementioned configuration, since a certain degree of range along the axial direction of the circumferential surface of the corrective body 1 supports the free edge B1 in a state of being in contact with the back side B10 of the free edge B1, it is possible to dispose the corrective body 1 without opening a hole in the free edge B1 and to prevent occurrence of breakage or cracking of the free edge B1 due to a point contact of the corrective body 1 to the free edge B1.

Further, by cutting the corrective body 1 to correspond to the width of the free edge B1, one kind of ingrown nail corrector A can cope with the different nail widths for each individual.

Further, since the corrective body 1 is inserted into the support hole 2 to be slidable in the axial direction, only the corrective body 1 is bent in a state in which the clamping portion 3 is fitted to the free edge B1, and by the repulsive force generated when returning from the deflection to a straight state, it is possible to correct the ingrown nail even if the clamping portion 3 is in the fixed state.

When the clamping portion 3 is fitted to the free edge B1, a repulsive force of the connecting portion 33 acts on the fixing plate 31 and the support plate 32 which clamp the free edge B1, and the contact protrusion 34 is latched on the latching groove B1a formed in the free edge B1. Accordingly, it is possible to enhance reliability of the attached state of the ingrown nail corrector A.

Further, since the tip 34b of the contact protrusion 34 is sharpened, even if the depth and width of the latching groove B1a are small, the tip 34b of the contact protrusion 34 is caught on the latching groove B1a. Accordingly, it is possible to prevent the detachment of the ingrown nail corrector A due to the deviation or dropout of the clamping portion 3 from the free edge B1. Further, even if the latching groove B1a is not formed, the tip 34b of the contact protrusion 34 is made to bite into the front side B13 of the free edge B1, which makes it possible to prevent detachment of the ingrown nail corrector A due to deviation or dropout of the clamping portion 3 from the free edge B1.

Further, since the contact protrusion 34 is formed as the inclined surface 34a by the above-described configuration, the sliding of the clamping portion 3 in the direction of fitting to the free edge B1 can be performed against the contact friction with which the fixing plate 31 and the tip 34b of the contact protrusion 34 come into contact with the free edge B1, by the repulsive force of the connecting portion 33.

Further, in the fitted state of the clamping portion 3, since the tip 34b of the contact protrusion 34 is latched on the latching groove B1a, sliding in the direction of retracting the clamping portion 3 from the free edge B1 is prevented, thereby making it possible to maintain the attached state of the ingrown nail corrector A.

Furthermore, even when the clamping portion 3 is fitted without forming the latching groove B1a, since the tip 34b of the contact protrusion 34 bites into the free edge B1 with respect to the sliding in the direction of extracting the clamping portion 3 from the free edge B1, sliding of the clamping portion 3 in the direction of being extracted from the free edge B1 is prevented, thereby making it possible to maintain the attached state of the ingrown nail corrector A.

Further, the contact protrusion 34 has a tapered shape that reaches the tip 34b, and both edges in the width direction (a right-left direction) are inclined edge portions 34c which are inclined. Therefore, when detaching the ingrown nail corrector A from the free edge B1, by causing the clamping portion 3 to slide in the width direction of the free edge B1, the inclined edge portion 34c of the contact protrusion 34 slides along the end portion B1b, while coming into contact with the end portion B1b of the latching groove B1a. Along with the sliding, the tip 34b of the contact protrusion 34 reaches the front side of the free edge B1 and can be detached by sliding as it is.

That is, the ingrown nail corrector A can be attached by fitting the clamping portion 3 to the free edge B1 from the tip B11, and can be detached by causing the clamping portion 3 to slide along the width direction of the free edge B1. Accordingly, it is possible to easily attach and detach the ingrown nail corrector A to and from the free edge B1 and to maintain the attached state, without bringing the clamping portion 3 into a fixed state with respect to the free edge B1.

Further, since the sliding of the clamping portion 3 at the time of detaching the ingrown nail corrector A can be performed without deforming or cutting the clamping portion 3, the ingrown nail corrector A can be reused. In the case of being reused in the nail B having a wide width, the used corrective body 1 may be detached from the support hole 2 and a new corrective body 1 may be inserted into the support hole 2. In the case of being reused in the nail B having a narrow width, the used corrective body 1 may be used as it is, and a portion protruding from the right and left edges B12, B12 of the free edge B1 may be cut.

Therefore, the ingrown nail corrector A of the present embodiment eliminates each problem such as prevention of cracking of the nail B at the time of attachment, a wide coping with the width of the nail B different for each individual, reduction in manufacturing cost, and maintenance of the attached state with respect to the free edge B1. Moreover, easiness of attachment and detachment with respect to the free edge B1 can be improved, and it is possible to reuse the ingrown nail corrector A.

Figure 5:
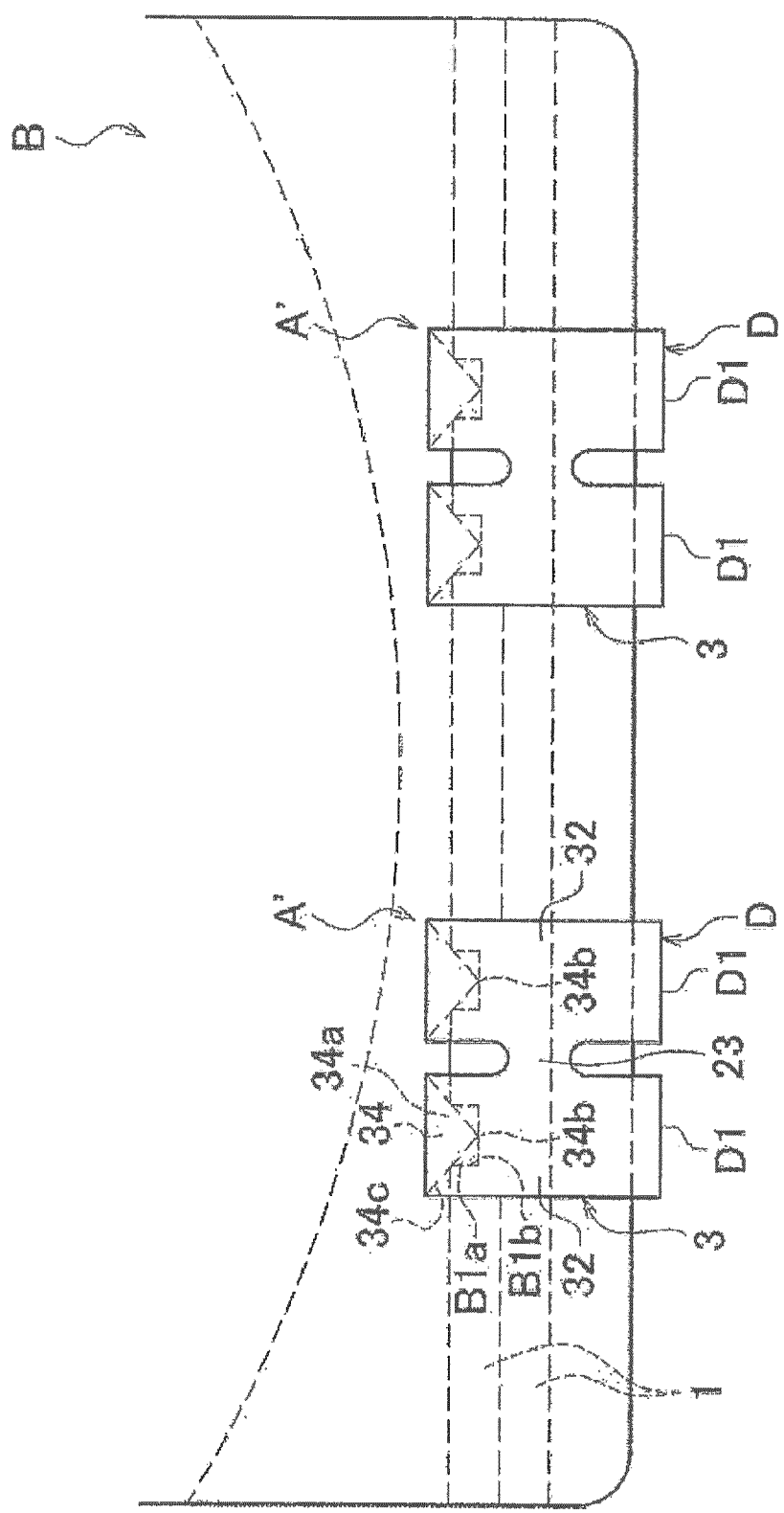
FIG. 5 is a plan view of an ingrown nail corrector according to a second embodiment of the invention.

Next, an ingrown nail corrector A' according to a second embodiment of the invention will be described with reference to FIG. 5. The description of the repeated contents of those of the ingrown nail corrector A of the first embodiment will not be provided by assigning the same reference numerals to the drawings.

The ingrown nail corrector A' is provided with two clips D, and the two clips D are attached by being fitted to the free edge B1 with an appropriate space between the clips D.

According to the ingrown nail corrector A', since the free edge B1 is clamped by the two clips D, it is possible to more reliably maintain the attached state with respect to the free edge B1, and moreover, it is suitable for being attached to the free edge B1 having a relatively wide nail width.

The proper use of the ingrown nail corrector A and the ingrown nail corrector A' can be variously used. That is, the ingrown nail corrector A is used for the free edge B1 having a narrow nail width, the ingrown nail corrector A' is used for the free edge B1 having a wide nail width as described above, the ingrown nail corrector A is used to quickly perform attachment to the free edge B1, and the ingrown nail corrector A' is used to more reliably perform attachment to the free edge B1, respectively.

Although the ingrown nail corrector A' is illustrated as having the two clips D, the number of clips D may be three or more and can be increased or decreased in accordance with the nail width.

Next, an ingrown nail corrector A" according to a third embodiment of the invention will be described with reference to FIGS. 6 and 7. The description of the repeated contents of the ingrown nail corrector A of the first embodiment and the ingrown nail corrector A' of the second embodiment will not be provided by assigning the same reference numerals to the drawings.

As described above, the ingrown nail corrector A and the ingrown nail corrector A' have the clip D having a pair of clip portions D1, but the ingrown nail corrector A' has a clip D' including one clip portion D1.

Figure 6:
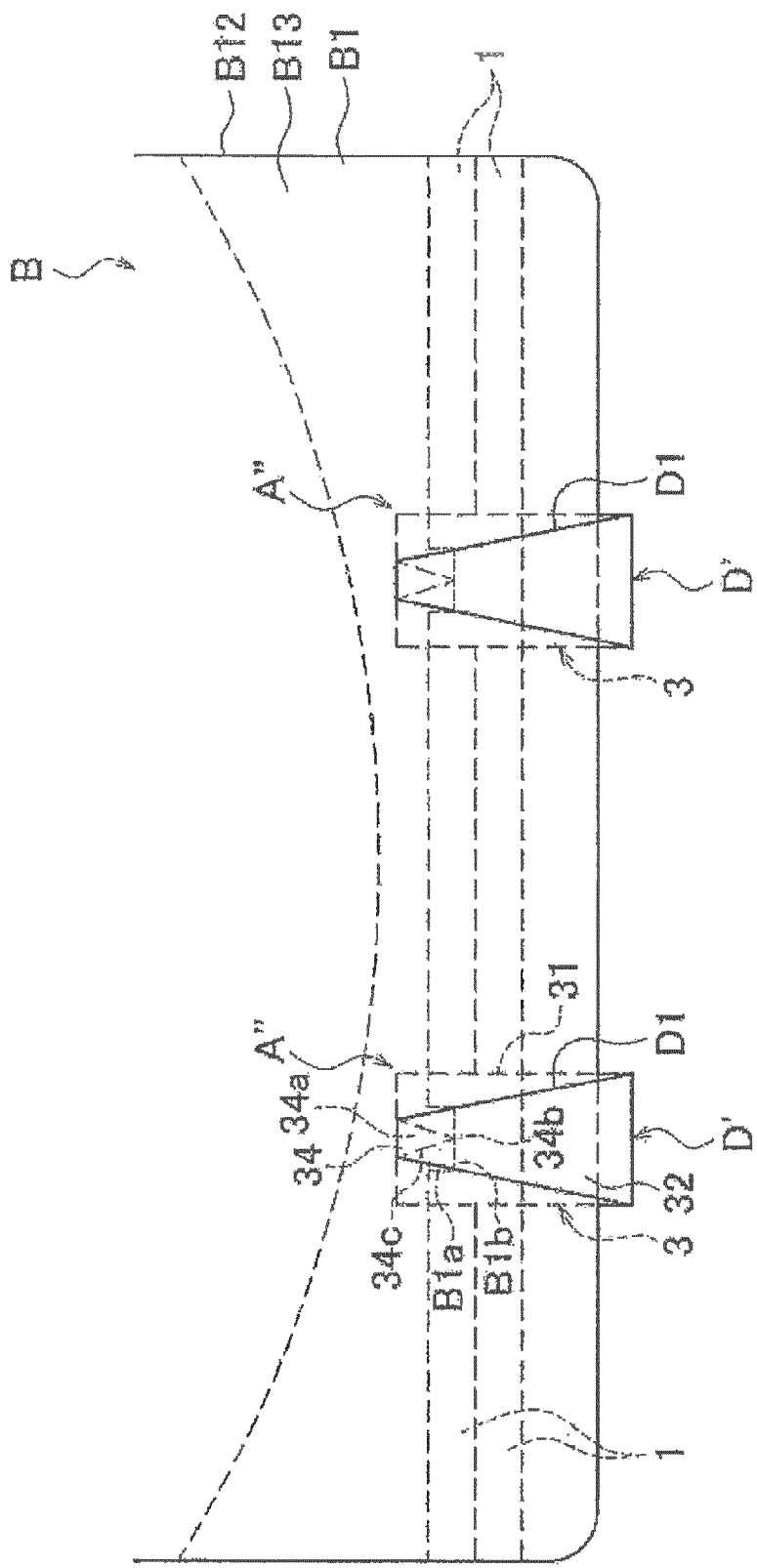
FIG. 6 is a plan view of an ingrown nail corrector according to a third embodiment of the invention.
Figure 7:
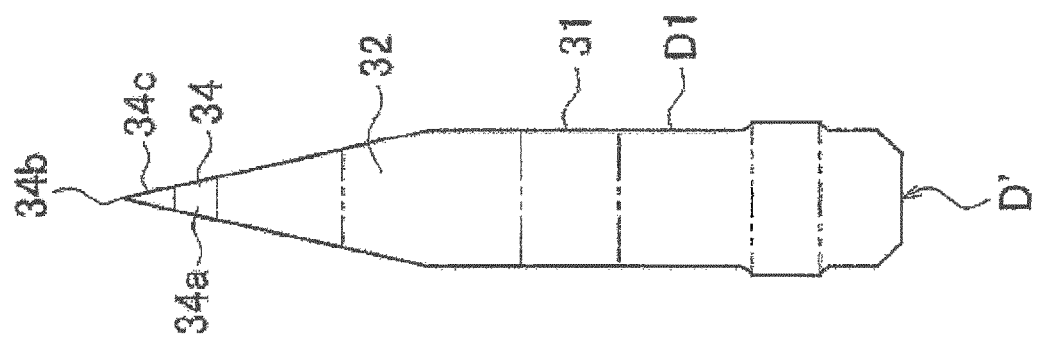
FIG. 7 is a plan view illustrating a state before bending.

As illustrated in FIGS. 6 and 7, the clip D' is configured such that the entire region of the support plate 32 in the clamping portion 3 is formed as a tapered shape from the end portion on the connecting portion 32 side to the end portion on the contact protrusion 34 side in a plan view, the contact protrusion 34 is formed continuously to the tapered shape of the support plate 32, and the contact protrusion 34 has a sharper angle than the contact protrusion 34 of the clip D.

Since the number of clip portion D1 is one, the ingrown nail corrector A" can quickly perform the attachment to the free edge B1, and in the attached state, it is possible to reduce the protruding portion of the ingrown nail corrector A" from the free edge B1.

Further, since the support plate 32 has a tapered shape in a plan view, the support plate 32 is in a state of being easily flexibly deformed in a direction of separating from the fixing plate 31 (a direction in which the insertion port 30 is expanded), and in particular, the side of the contact protrusion 34 is easily flexibly deformed.

That is, at the time of attachment of the ingrown nail corrector A" to the free edge B1, since the insertion port 30 is expanded by flexural deformation of the support plate 32, the force required for expansion decreases, the repulsive force returning from the expansion also decreases, and the contact pressure of the contact protrusion 34 to the free edge B1 during insertion is also lowered. Accordingly, the insertion of the free edge B1 into the insertion port 30 can be smoothly performed.

Furthermore, since the tip of the contact protrusion 34 has an acute angle, the width of the latching groove B1a can be narrowed, and even if the depth of the latching groove B1a is shallow, it is possible to maintain the reliability of the latched state of the contact protrusion 34 with respect to the latching groove B1a. Further, even if the health condition of the free edge B1 is poor, it is possible to suppress breakage of the free edge B1 at the time of forming the latching groove B1a.

Figure 8:
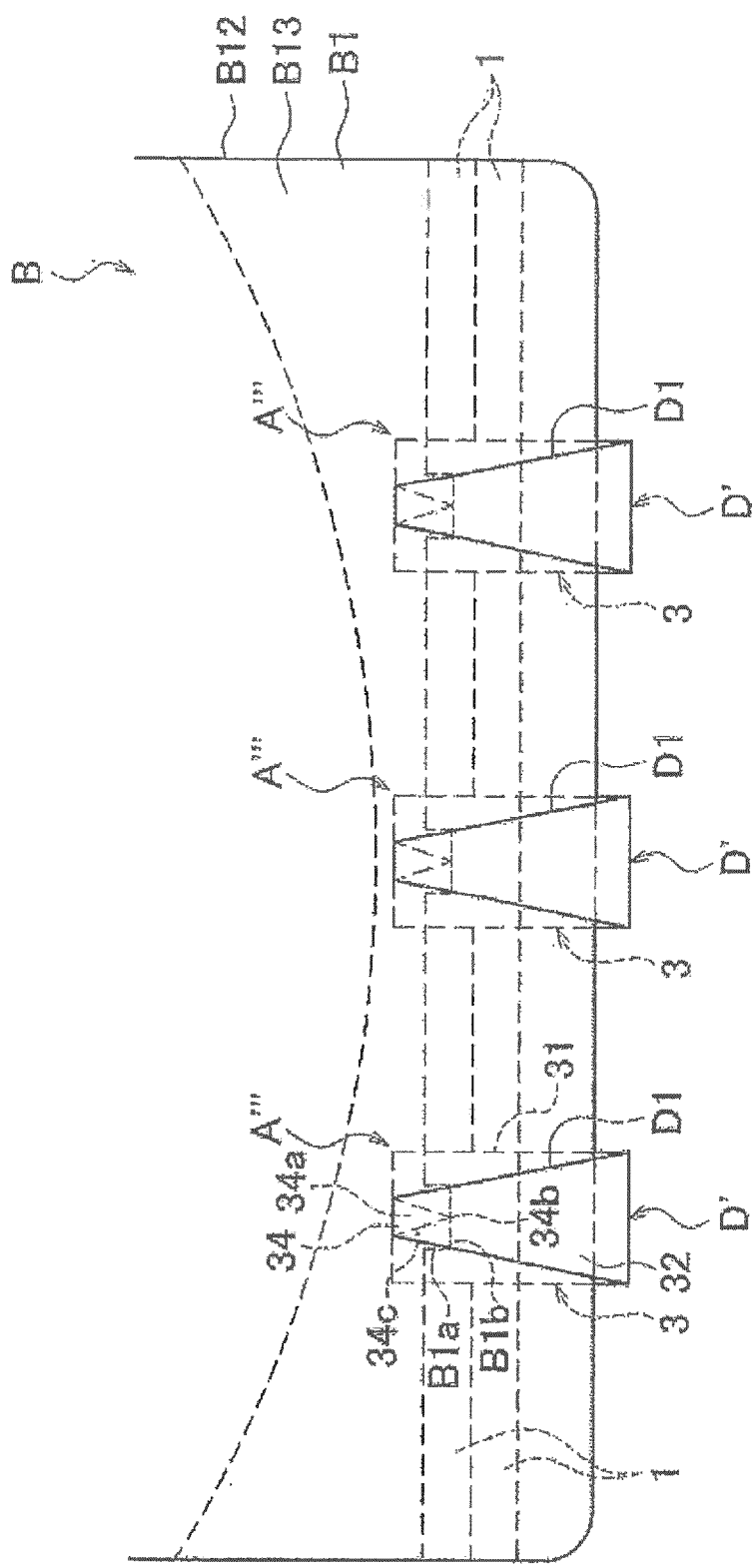
FIG. 8 is a plan view of an ingrown nail corrector according to a fourth embodiment of the invention.
Figure 9:
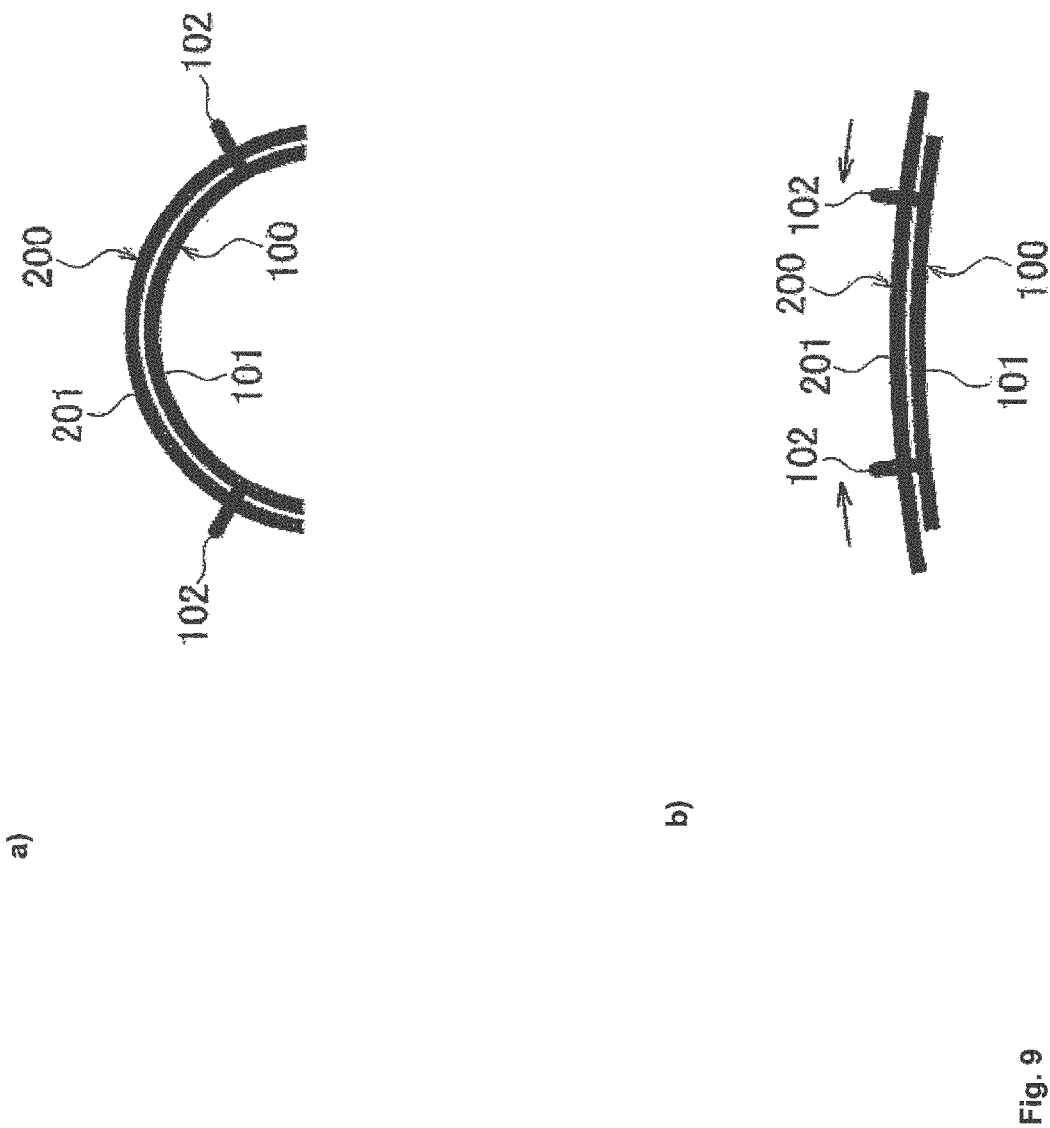
FIG. 9 is a diagram illustrating a correction operation of a conventional ingrown nail corrector.

Next, an ingrown nail corrector A'" according to a fourth embodiment of the invention will be described with reference to FIG. 8. The ingrown nail corrector A'" of this embodiment is provided with three clips D' of the third embodiment. The description of the repeated parts of the third embodiment will not be provided by assigning the same reference numerals to the drawings.

The ingrown nail corrector A'" of the fourth embodiment has the same effect as the ingrown nail corrector A" of the third embodiment, and since the three clips D' are provided, it is possible to more reliably maintain the attached state to the free edge B1.

The number of clips D' can be increased or decreased in accordance with the width of the free edge B1. Further, from the viewpoint of maintaining the attached state to the free edge B1, it is preferable to provide at least two clips D'.

In the invention, the ingrown nail corrector A having no contact protrusion 34 may be used. In this case, in order to more reliably maintain the attached state to the free edge B1, the repulsive force of the connecting portion 33 may be strengthened to enhance the clamping force of the clamping portion 3, and the clamping portion 3 may be fixed to the free edge B1 with an adhesive or an adhesive tape.

The invention is not limited to the illustrated embodiments, and can be implemented with configurations within the scope that does not depart from the contents described in the respective claims.

EXPLANATIONS OF LETTERS OR NUMERALS

A ingrown nail corrector
A' ingrown nail corrector
A" ingrown nail corrector
A'" ingrown nail corrector
B nail
B1 free edge
1 corrective body
2 support hole 3 clamping portion
B2 end edge
B3 end edge
30 insertion port
31 fixing plate
32 support plate
33 connecting portion
34 contact protrusion
34a inclined surface
34b tip
B1a latching groove

The invention claimed is:

1. An ingrown nail corrector which is configured to attach to a tip of a free edge of a nail to correct an ingrown nail, the ingrown nail corrector comprising a corrective body, a support hole, a clamping portion and a contact protrusion,
wherein a shape of the contact protrusion consists of a plate,
wherein the corrective body is formed to have a length in a longitudinal direction to be equal to or larger than a nail width of the free edge, using a material having elasticity in which a repulsive force is generated against a force in a direction of flexure,
the support hole has an axis parallel to the longitudinal direction of the corrective body,
the corrective body is inserted in a freely slidable manner with the longitudinal direction of the corrective body parallel to an axis of the support hole,
the clamping portion includes:
a fixing plate having one end protruding to be fixed to the support hole with a width direction parallel to the axis of the support hole,
a support plate which is disposed to face the fixing plate while being spaced apart in a thickness direction of the fixing plate with the width direction thereof parallel to the axis of the support hole, the support plate having a tapered shape in a plan view,
an insertion port secured between the fixing plate and an end portion of the support plate on a support hole side, and being configured for insertion of the tip of the free edge of the nail thereinto, and
a connecting portion which connects the fixing plate and the support plate at a protruding side end portion of the fixing plate, and has elasticity in which a repulsive force is generated against a force in a direction in which the support plate separates from the fixing plate with expansion of the insertion port,
the contact protrusion plate is integrally formed with the support plate or the fixing plate and formed so as to be located between the support plate and the fixing plate, whereby a front edge portion of the contact protrusion plate is caught in a latching groove provided on a front side of the free edge at the time of attachment,
a tip of the contact protrusion plate has an acute angle in the plan view, and
the contact protrusion plate is formed as an inclined surface which gradually approaches a side of the fixing plate as it goes from the end portion of the support plate on a side of the insertion port to a side of the connecting portion and inclines to narrow a space between the fixing plate and the support plate,
the contact protrusion plate is formed continuously to the tapered shape of the support plate.

2. The ingrown nail corrector according to claim 1, wherein the contact protrusion plate is formed in a tapered shape from both edge portions in the width direction toward the end portion on the protruding side.

3. The ingrown nail corrector according to claim 1, wherein the contact protrusion plate is formed in a tapered shape from both edge portions in the width direction toward the end portion on the protruding side, and
the contact protrusion plate has an inclined surface which is inclined in a direction of narrowing a gap between the fixing plate and the support plate from the insertion port side of the fixing plate or the support plate toward the connecting portion side.

4. The ingrown nail corrector according to claim 1, wherein the corrective body is covered with a resin film.

5. An ingrown nail corrector which is configured to attach to a tip of a free edge of a nail to correct an ingrown nail, the ingrown nail corrector comprising a corrective body, a support hole, a clamping portion and a contact protrusion plate, wherein a shape of the contact protrusion comprises a plate, wherein the corrective body is formed to have a length in a longitudinal direction to be equal to or larger than a nail width of the free edge, using a material having elasticity in which a repulsive force is generated against a force in a direction of flexure, the support hole has an axis parallel to the longitudinal direction of the corrective body, the corrective body is inserted in a freely slidable manner with the longitudinal direction of the corrective body parallel to an axis of the support hole, the clamping portion includes: a fixing plate having one end protruding to be fixed to the support hole with a width direction parallel to the axis of the support hole, a support plate which is disposed to face the fixing plate while being spaced apart in a thickness direction of the fixing plate with the width direction thereof parallel to the axis of the support hole, the support plate having a tapered shape in a plan view, an insertion port secured between the fixing plate and an end portion of the support plate on a support hole side, and being configured for insertion of the tip of the free edge of the nail thereinto, and a connecting portion which connects the fixing plate and the support plate at a protruding side end portion of the fixing plate, and has elasticity in which a repulsive force is generated against a force in a direction in which the support plate separates from the fixing plate with expansion of the insertion port, the contact protrusion plate is integrally formed with the support plate or the fixing plate and formed so as to be located between the support plate and the fixing plate, whereby a front edge portion of the contact protrusion plate is caught in a latching groove provided on a front side of the free edge at the time of attachment, a tip of the contact protrusion plate has an acute angle in the plan view, and the contact protrusion plate is formed as an inclined surface which gradually approaches a side of the fixing plate as it goes from the end portion of the support plate on a side of the insertion port to a side of the connecting portion and inclines to narrow a space between the fixing plate and the support plate, the contact protrusion plate is formed continuously to the tapered shape of the support plate; wherein corresponding facing surfaces of the contact protrusion plate and the support plate are spaced apart from one another.

* * * * *